(12) United States Patent
Baltzer

(10) Patent No.: US 9,997,346 B1
(45) Date of Patent: Jun. 12, 2018

(54) ELECTRON SPECTROMETER

(71) Applicant: MB Scientific AB, Uppsala (SE)

(72) Inventor: Peter Baltzer, Uppsala (SE)

(73) Assignee: MB Scientific AB, Uppsala (SE)

( * ) Notice: Subject to any disclaimer, the term of this patent is extended or adjusted under 35 U.S.C. 154(b) by 0 days. days.

(21) Appl. No.: 15/639,477

(22) Filed: Jun. 30, 2017

(51) Int. Cl.
*H01J 49/44* (2006.01)
*H01J 49/06* (2006.01)

(52) U.S. Cl.
CPC ............ *H01J 49/44* (2013.01); *H01J 49/067* (2013.01); *G01N 2223/32* (2013.01)

(58) Field of Classification Search
CPC ..... H01J 49/067; H01J 49/44; G01N 2223/32
See application file for complete search history.

(56) References Cited

U.S. PATENT DOCUMENTS

| 3,766,381 A | 10/1973 | Watson |
| 6,005,245 A | 12/1999 | Sakairi et al. |
| 2010/0176565 A1* | 7/2010 | Farrelly ................. A63C 17/01 280/11.27 |
| 2010/0185309 A1* | 7/2010 | Ohiaeri .............. G06Q 30/0603 700/98 |
| 2010/0266935 A1* | 10/2010 | Albert .................. B29C 43/222 430/2 |
| 2010/0279583 A1* | 11/2010 | Laurienzo ............. A63H 17/26 446/467 |

FOREIGN PATENT DOCUMENTS

| WO | 2008010777 A1 | 1/2008 |
| WO | 2013133739 A1 | 9/2013 |

OTHER PUBLICATIONS

International Type Search Report for National Application 1650967-1, dated Jul. 1, 2016—5 Pages.
Kozina et al., "Development of Hard X-Ray Photoelectron SPLEED-based Spectrometer Applicable for Probing of Buried Magnetic Layer Valence States", Journal of Electron Spectroscopy and Related Phenomena., May 2016, vol. 211, p. 12-18.
Lindblad et al., A Mutli Purpose Source Chamber at the PLEIADES Beamline at SOLEIL for Spectroscopic Studies of Isolated Species: Cold Molecules, Clusters, and Nanoparticles. Review of Scientific Instruments, Nov. 2013, vol. 84, No. 11, p. 113105-1-113105-11.
Mårtensson et al., "A Very High Resolution Electron Spectrometer", Journal of Electron Spectroscopy and Related Phenomena., Dec. 1994, vol. 70, p. 117-128.
Reinhold-Lopez et al., Simultaneous in situ Raman Monitoring of the Solid and Gas Phases During the Formation and Growth of Carbon Nanostructures Inside a Cold Wall CCVD Reactor, Carbon, Jun. 2014, vol. 78, p. 164-180.

(Continued)

*Primary Examiner* — Eliza Osenbaugh-Stewar
(74) *Attorney, Agent, or Firm* — RatnerPrestia

(57) ABSTRACT

A charged particle spectrometer of hemispherical analyzer type for analyzing a particle emitting sample, the spectrometer comprising at least a first mechanism configured to move at least a part of the lens with respect to the axis between the sample spot and the analyzer entrance in a coordinate direction synchronously with a deflection of the particle beam.

16 Claims, 21 Drawing Sheets

(56) References Cited

OTHER PUBLICATIONS

Rossnagel et al., "A High Performance Angle-Resolving Electron Spectrometer", Nuclear Instruments and Methods in Physical Research A, Jul. 2001, vol. 467-468, p. 1485-1488.

Muro et al., "In Situ Positioning of a Few Hundred Micrometer-Sized Cleaved Surfaces for Soft-X-Ray Angle-Resolved Photoemission Spectroscopy by Use of an Optical Microscope", Review of Scientific Instruments, May 2009, vol. 80, p. 53901-1-53901-4.

* cited by examiner

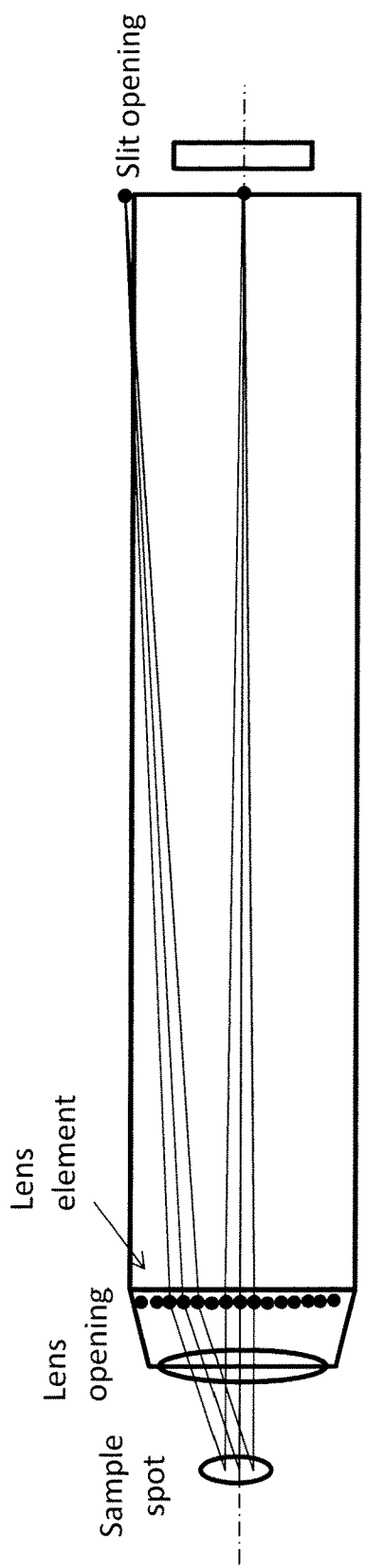
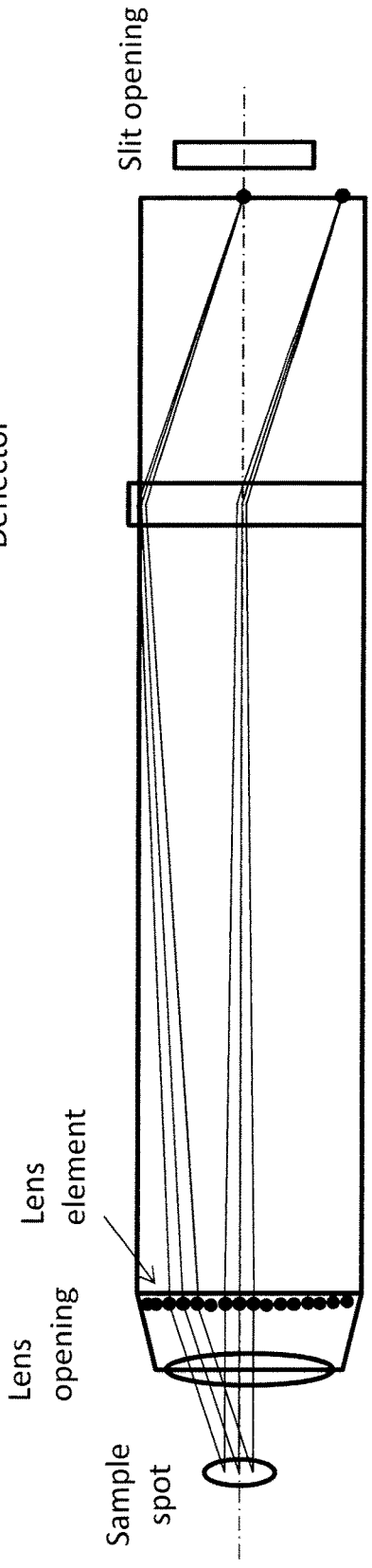
Fig. 6a
Fig. 6b

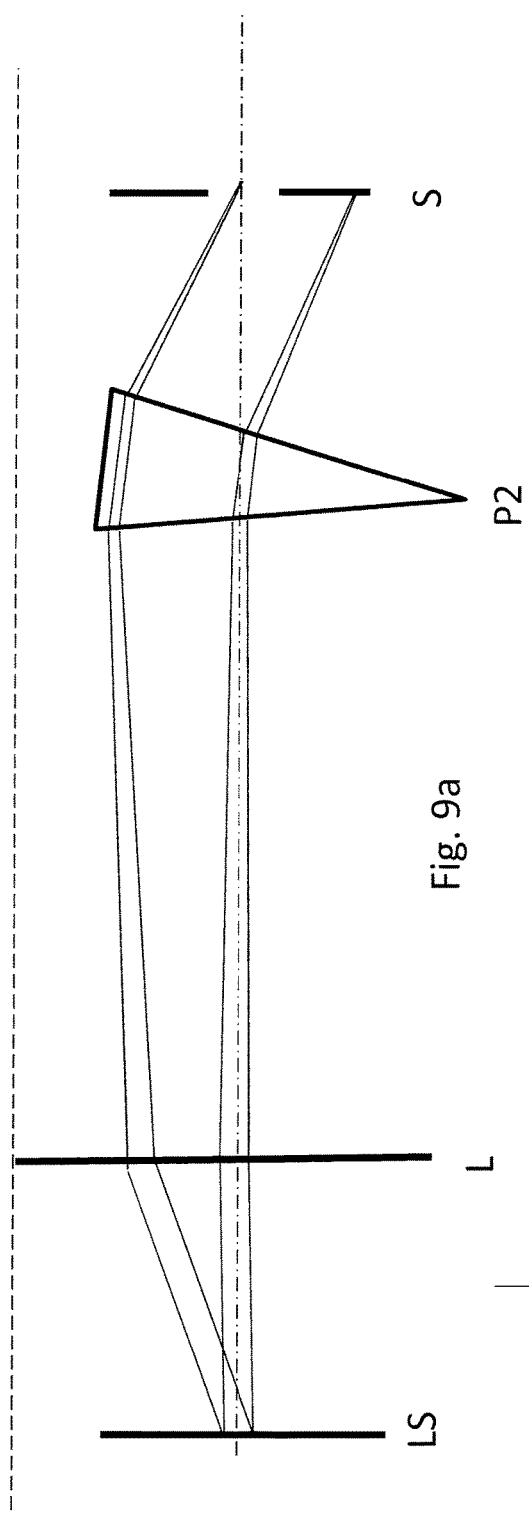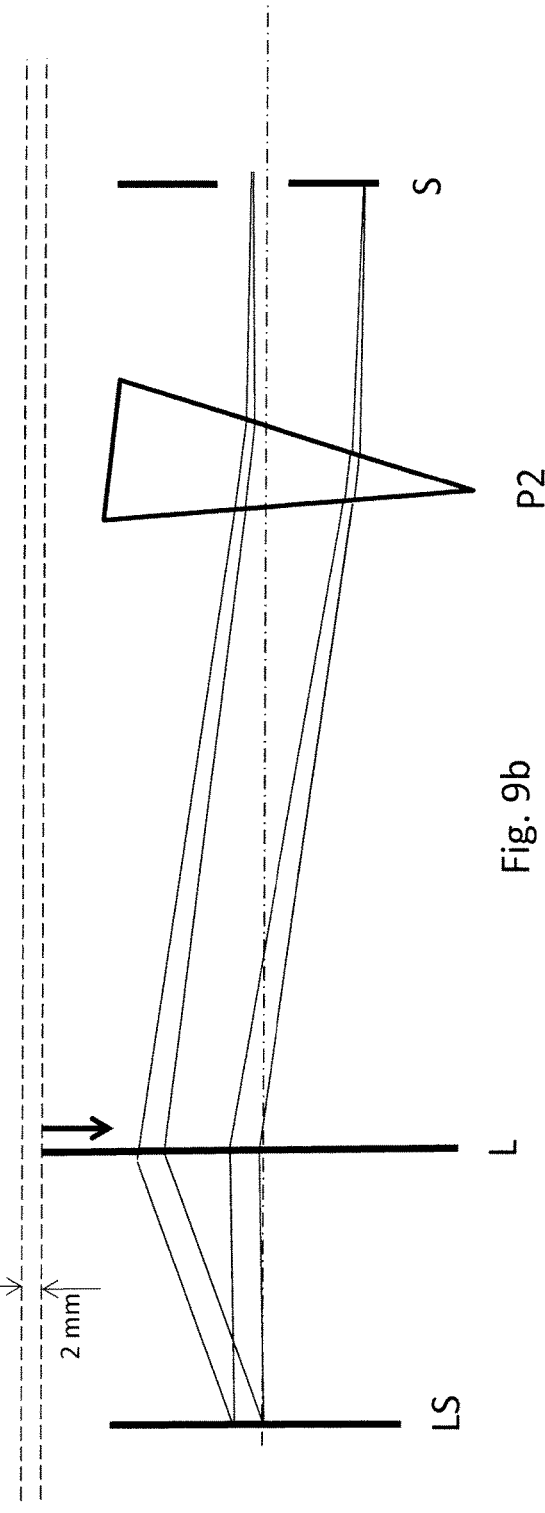
Fig. 9a
Fig. 9b

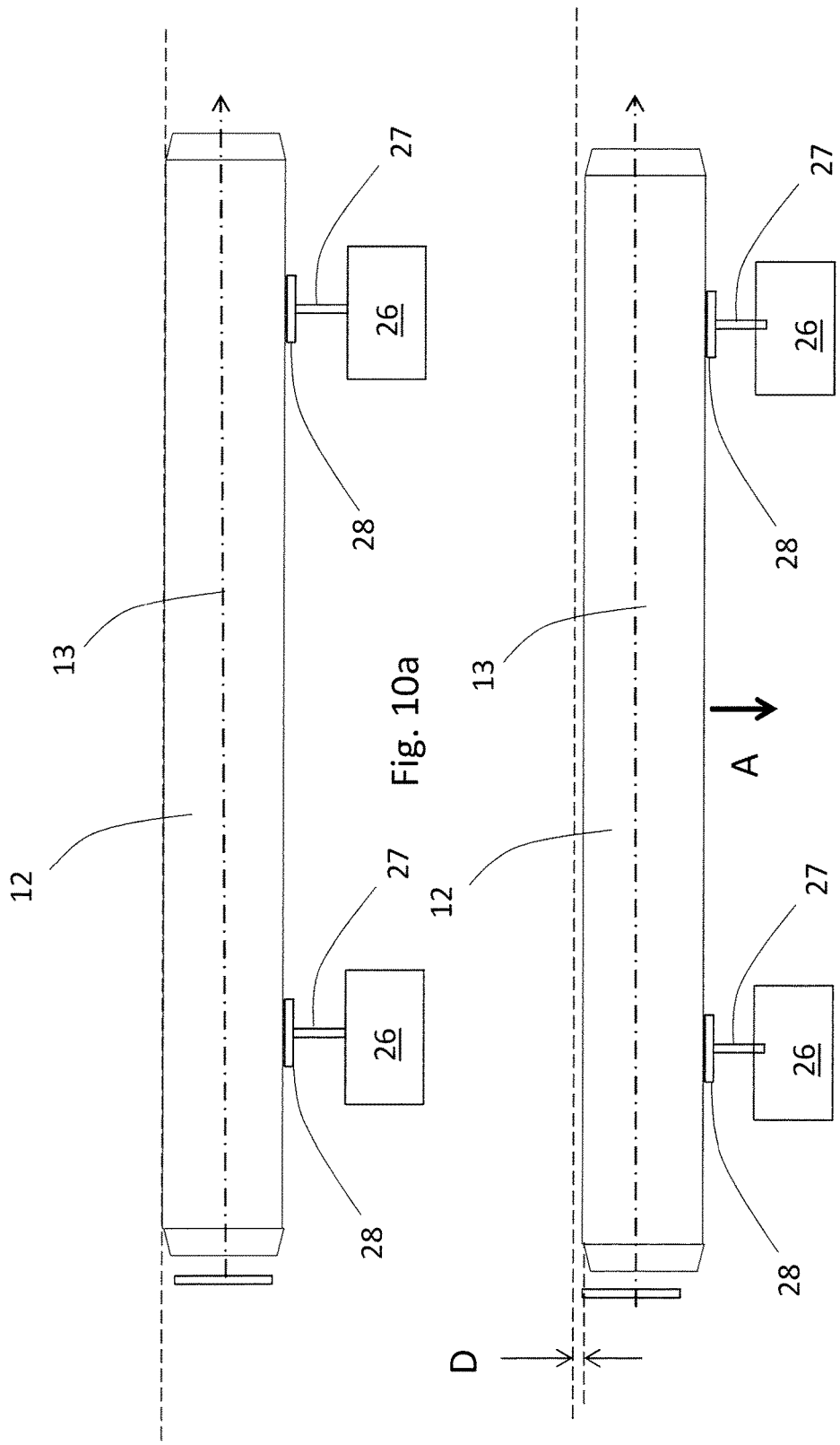

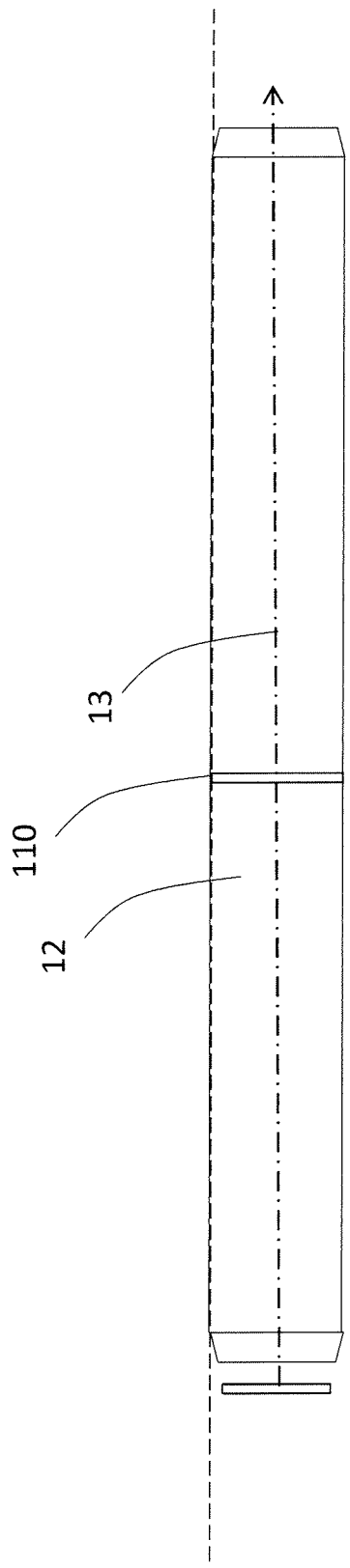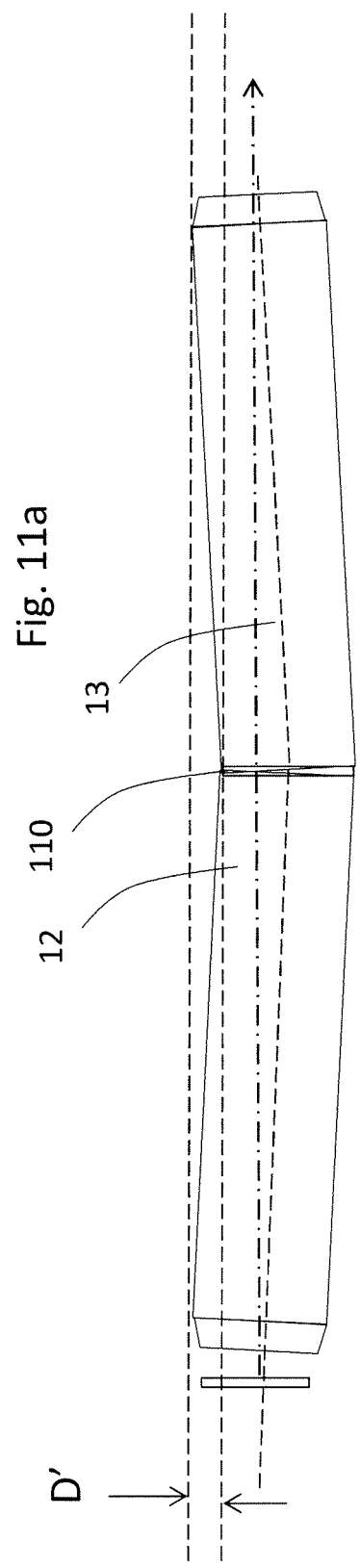

ELECTRON SPECTROMETER

The present invention relates to electron spectrometers in general, and in particular to a novel means and method for operating in angular mode.

BACKGROUND OF THE INVENTION

In a photo-electron spectrometer of hemispherical analyzer type, a central component is the measurement region in which the energies of the electrons are analysed. The measurement region is formed by two concentric hemispheres, mounted on a base plate, and with an electrostatic field applied between them. The electrons enter the measurement region through an entrance and electrons entering the region between the hemispheres with a direction close to perpendicular to the base plate are deflected by the electrostatic field, and those electrons having a kinetic energy within a certain range defined by the deflecting field will reach a detector arrangement after having travelled through a half circle. In a typical instrument, the electrons are transported from their source (typically a sample that emits electrons after excitation with photons, electrons or other particles) to the entrance of the hemispheres by an electrostatic lens system comprising a plurality of lenses having a common and substantially straight optical axis.

The lens system and the detector arrangement will only accept electrons which are emitted within a limited area perpendicular to the lens axis and within a limited angular range. Furthermore, the source has to be positioned within a narrow range in the z-direction to achieve the best properties (in terms of sensitivity and resolution). This necessitates mounting the sample on a manipulator allowing both translations and rotations in all coordinate directions, i.e. six degrees of freedom.

In many applications of for example Angle Resolved Photoelectron Spectroscopy (ARPES) a complete measurement requires full detection of a solid angle with a total cone opening of 30 degrees from a well aligned sample. Depending on sample and excitation energy/kinetic energy the required angular range may vary. The angle resolution requirements also varies with application but typically range from 1 degree down to better than 0.1 degrees. In energy resolution the desired span is from 0.5 eV down to 0.5 meV depending on application. In order to achieve a high resolution measurement the analyser arrangement must have sufficient angular and energy resolution, but since the hemispherical analyser arrangement only accepts electrons emitted within a limited angular range perpendicular to the lens axis, the sample manipulator must have very high precision movements and repeatability. The manipulator is needed to accurately rotate and tilt the sample to build up the complete 30 degree solid angle data set.

However, in recent years the illumination systems have reached a much higher level of spatial resolution which means that extremely minute crystallites can be observed. Thereby the manipulation, i.e. rotation of the sample becomes very difficult.

One way of eliminating the sample manipulation is to provide a second deflector inside the lens and close to the first deflector in order to bring the electron beam at the entrance to the measurement region in alignment with the optical axis of the lens.

Spectrometers provided with such deflectors inside the lens have been sold by VG Scienta AB.

Despite the fact that this system eliminated the need for sample manipulation, it still suffers from some distortion in the recorded images.

SUMMARY OF THE INVENTION

In order to improve the quality of the recorded images, the present inventor has devised a novel device which also eliminates the need for sample manipulation and in addition provides less distortion.

Thereby there is provided a charged particle spectrometer of hemispherical analyzer type for analyzing a particle emitting sample. The spectrometer comprises a measurement region having an entrance allowing said particles to enter the measurement region; a lens system for forming a particle beam of said charged particles and transporting the particles between said particle emitting sample and said entrance of the measurement region, said lens system having a substantially straight optical axis; a deflector arrangement in the lens comprising a deflector configured to deflect the particle beam in at least one coordinate direction (x, y) perpendicular to the optical axis of the lens system before entrance of the particle beam into the measurement region, a detector arrangement for detecting the positions of the charged particles in the measurement region, wherein the detector arrangement is configured to determine the positions of the charged particles in two dimensions, one of which is indicative of the energies of the particles and one of which is indicative of the start directions or start positions of the particles.

The inventive idea is to displace (i.e. move from one position to a slightly different position, incrementally) at least a part of the lens with respect to the axis between the sample spot and the analyser entrance in at least a first coordinate direction and then to subject the particle beam to one single deflection inside the lens system. The displacement is made synchronously with the deflection of the particle beam, whereby the trajectories of said charged particles will enter the measurement region. The particle beam will thus enter the lens "off-axis", which causes the beam to be focused at a different point.

The term "nominal position" of the lens or lens axis should be taken to mean a situation where a particle beam running along a horizontal line from the sample spot to be studied follows the lens axis and is focused on the entrance slit at a point coinciding with the lens axis.

In particular it should be noted that beams having start directions deviating from the horizontal that would be focused above the entrance slit before the measurement region in the nominal position of the lens, can be made to be focused at a point below the slit if the displacement is made in an appropriate manner.

Therefore, it will suffice with one single deflection stage inside the lens in order to bring the beam back to horizontal, i.e. aligned, or at least parallel, with a nominal optical axis.

There are several possible ways of achieving this effect, e.g. tilting the lens, bending the lens at some point along its length, or moving the entire lens in the coordinate direction in question.

In one embodiment the lens is suspended in a multidirectional pivot point at that end of the lens that is adjacent to the entrance of the measurement region such that the lens can be tilted around the pivot point in said coordinate direction (x, y).

There is also provided at least a first tilting mechanism configured to tilt the lens in said coordinate direction synchronously with a deflection of the particle beam.

In one embodiment of the spectrometer the mechanism for tilting the lens comprises a motor, an actuator rod connected to the motor, and a spring loaded device arranged to keep the lens in contact with the tilting mechanism.

Preferably, the spectrometer comprises a further tilting mechanism arranged at right angles to the first tilting mechanism, configured to tilt the lens in a second coordinate direction (x, y) synchronously with a deflection of the particle beam, whereby the spring loaded device is arranged symmetrically opposite the first and second tilting mechanisms at an angular distance of about 135°.

In another embodiment the entire lens is suspended in a mechanism that allows it be moved in a desired coordinate direction.

In still another embodiment the lens is subdivided in a plurality of lens elements, but at least two lens elements, which are connected in a manner such that the lens can be bent at the position where the elements are joined.

All of the above embodiments achieve the same result to enable the particle beam to be realigned by using one single deflector unit.

In a second aspect the invention provides a method for determining at least one parameter related to charged particles emitted from a particle emitting sample, comprising the steps of forming a particle beam of said charged particles and transporting the particles between said particle emitting sample and an entrance of a measurement region by means of a lens system having a substantially straight optical axis, said lens being suspended in a multidirectional pivot point at that end of the lens that is adjacent to the entrance of the measurement region such that the lens can be tilted in said coordinate direction (x, y); deflecting the particle beam in at least a first coordinate direction (x, y) perpendicular to the optical axis of the lens system before entrance of the particle beam into the measurement region,
detecting the positions of said charged particles in said measurement region, the positions being indicative of said at least one parameter, detecting the positions of the charged particles involves detection of the positions in two dimensions, one of which is indicative of the energies of the particles and one of which is indicative of the start directions or start positions of the particles.

In one embodiment the lens is tilted in said coordinate direction synchronously with the deflection of the particle beam, whereby the trajectories of said charged particles will enter the measurement region.

In another embodiment the entire lens is moved, and in a further embodiment the lens is bent.

BRIEF DESCRIPTION OF THE DRAWINGS

Further scope of applicability of the present invention will become apparent from the detailed description given hereinafter and the accompanying drawings which are given by way of illustration only, and thus not to be considered limiting on the present invention, and wherein FIG. 1 schematically illustrates a part of an electron spectrometer embodying a novel feature for operation in angular mode;

FIG. 6a shows the particle beams in a lens without a deflector;

FIG. 6b shows the particle beams in a lens with a deflector;

FIG. 9a illustrates tilting a lens and a single deflection using a prism;

FIG. 9b shows the same setup as in FIG. 9a where the lens L has been moved downwards a small distance;

FIG. 10a illustrates a mechanism for moving the entire lens wherein the lens is in a nominal position;

FIG. 10b shows the same setup as in FIG. 10a where the lens L has been moved downwards a small distance;

FIG. 11a illustrates the lens in nominal position;

FIG. 11b illustrates bending the lens;

DETAILED DESCRIPTION OF PREFERRED EMBODIMENTS

Figure 1:
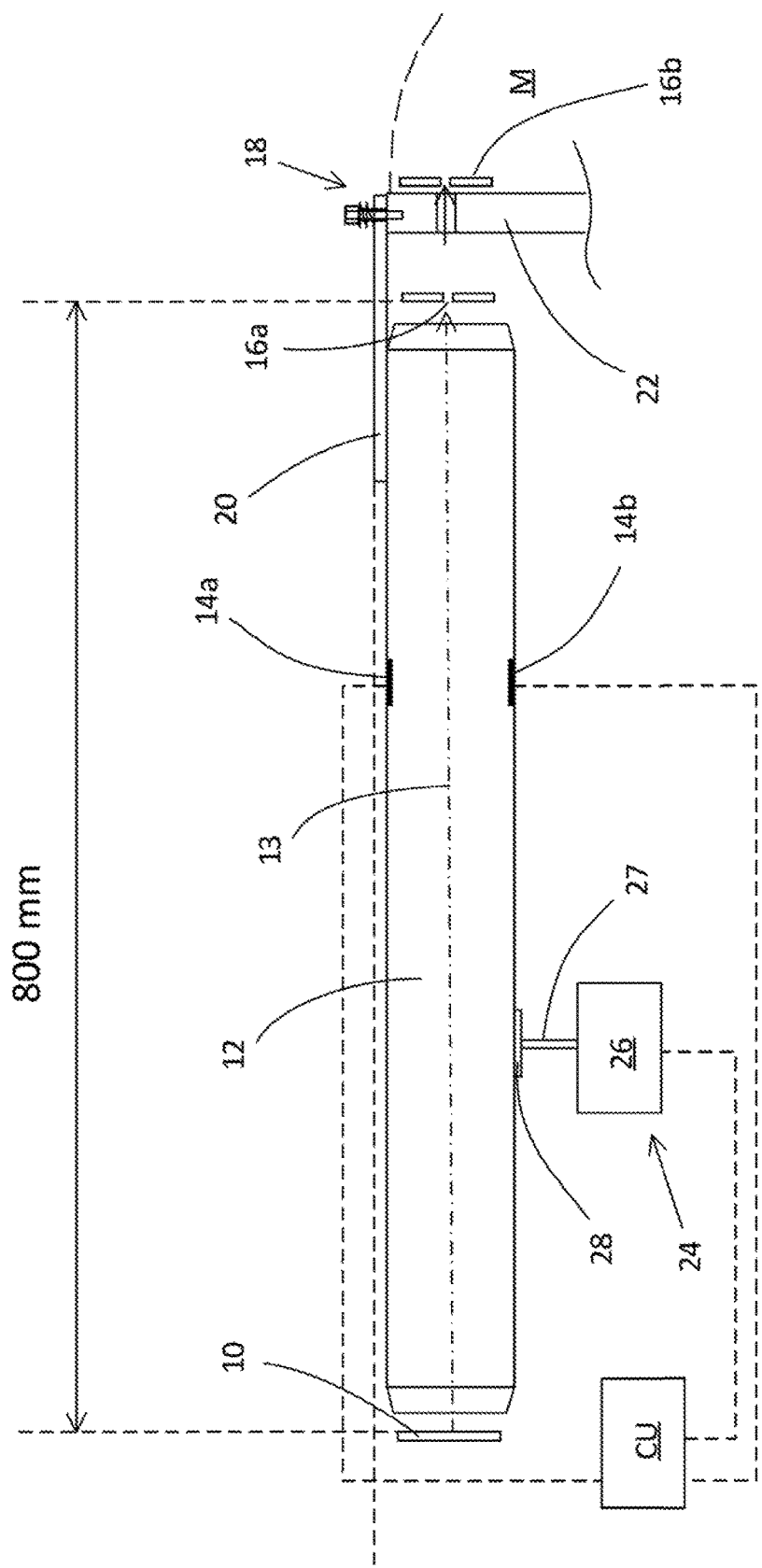

FIG. 1 illustrates schematically a part of an electron spectrometer embodying the invention, namely the sample 10, the electron lens 12 having an optical axis 13, a pair of deflectors 14a, 14b, an entrance slit 16a to the measurement region of a hemispherical analyser M (only indicated with a broken line), a hinge mechanism 18 suspending the lens 12 in a multi-directional pivot point, via a beam 20 rigidly attached to the body of the lens 12. The hinge 18 is attached to the base plate 22 of the hemispherical analyser M. Inside the measurement region there is a second slit 16b.

The novelty of the apparatus resides in a preferred embodiment in a tilting mechanism 24. This mechanism in a first embodiment comprises a motor 26, preferably an electric motor, preferably a stepper motor.

The motor is controlled by a control unit CU that also controls the voltages on the deflectors 14a, 14b, the control being schematically indicated with broken lines, and will be described further below.

The motor 26 is configured to actuate a pushing member 27, capable of movement in a vertical direction. The pushing member 27 is suitably an actuator rod to the upper end of which is attached a support plate 28 on which the lens 12 rests.

Figure 2:
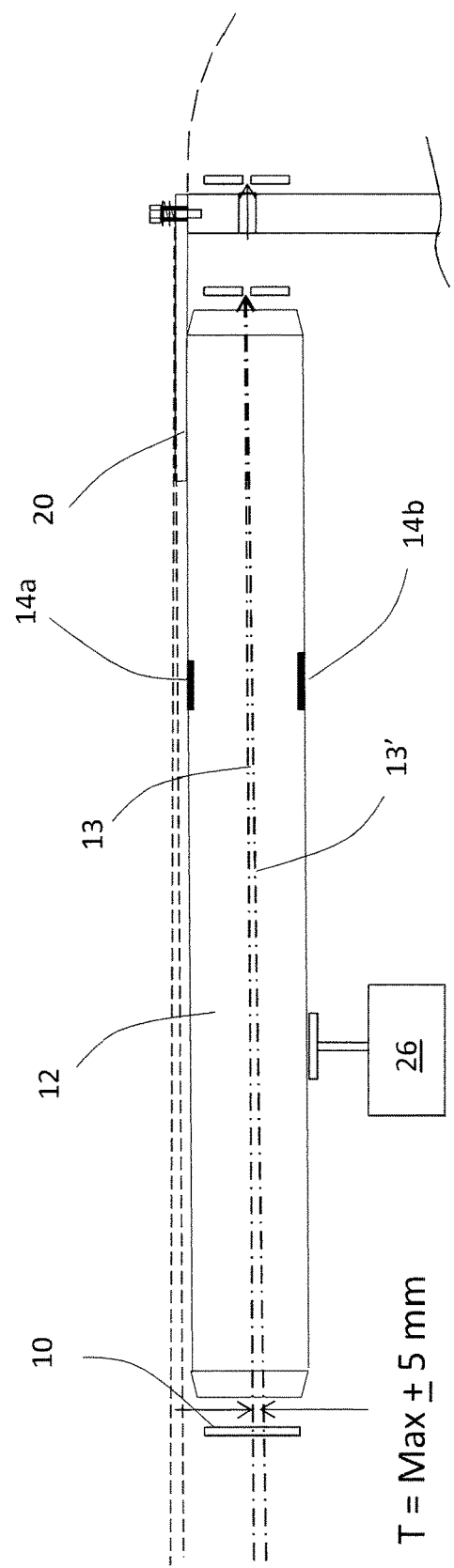
FIG. 2 shows the same apparatus as in FIG. 1 wherein the lens has been slightly tilted in accordance with the novel feature.

In FIG. 2 the lens 12 has been slightly tilted from the horizontal, i.e. the entrance region to the lens 12 has been moved a small distance (maximum about 5 mm) from the horizontal. This is clearly seen as the optical axis of the lens deviates 13' from its nominal position 13.

Figure 3:
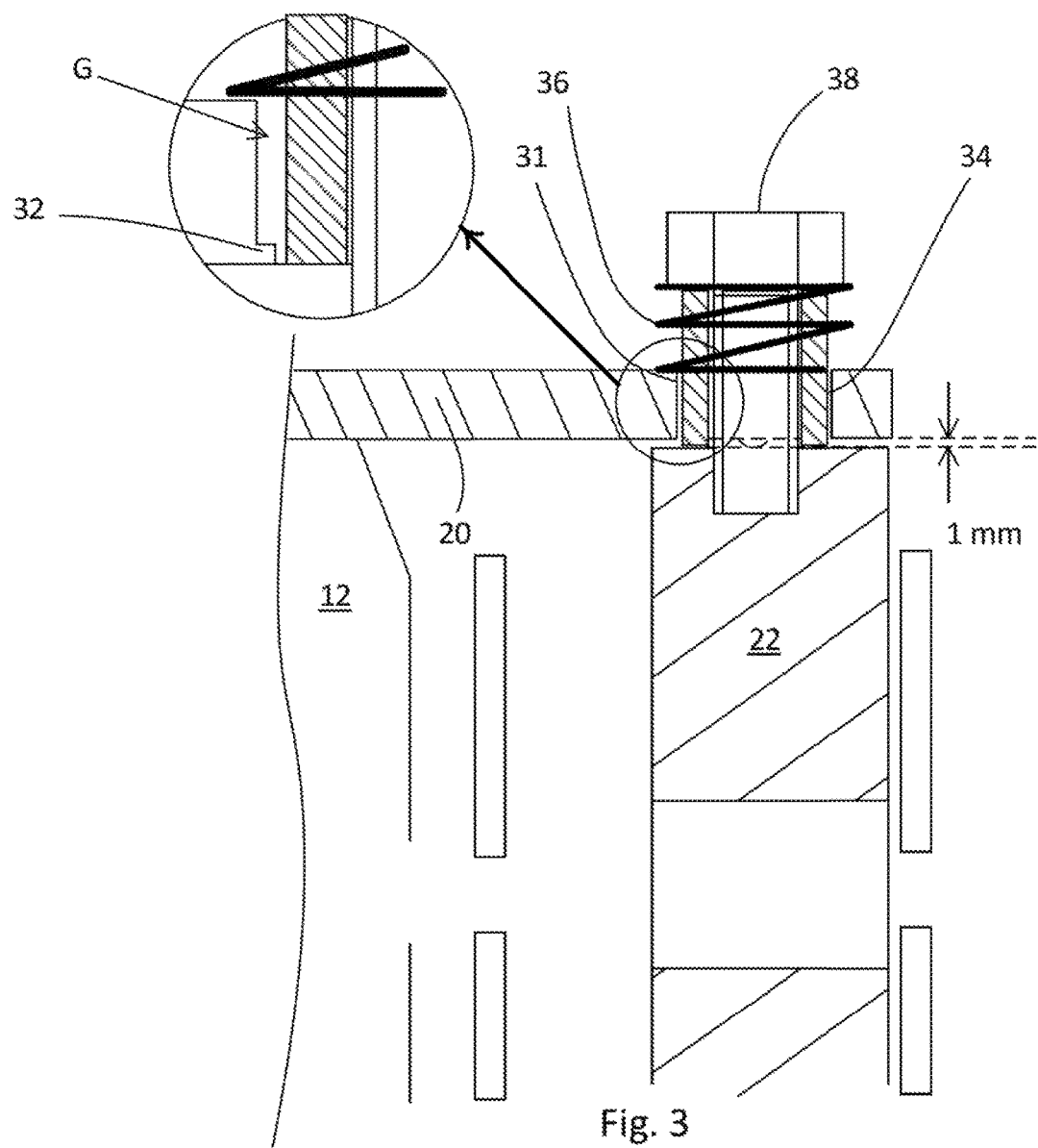
FIG. 3 illustrates a multi-directional hinge.

The hinge mechanism 18 will now be described briefly with reference to FIG. 3. Such hinge mechanisms are provided on most electron spectrometers according to prior art and used for adjustment purposes, and form no part of the invention per se.

The hinge mechanism comprises a beam member 20 rigidly mounted (e.g. welded or bolted) to the lens body 12. The beam 20 protrudes out from the proximal end of the lens body. At the end of the protruding portion of the beam 20 the beam has a through-hole 31. The through-hole has a wider diameter at the top than at the bottom, see the magnified encircled portion, i.e. there is a small step 32 at the lowermost part of the hole. Note that the dimensions are not to scale. In the hole there is a sleeve member 34. Thus, due to the step 32 there will be a small circumferential gap G between sleeve 34 and the inner circumference of the through-hole 31. Resting on the periphery of the sleeve 34 there is a spring member 36, suitably a cup spring. A bolt or screw 38 is anchored in the base plate 22, and when tightened the screw and spring will exert a strong downward force which ascertains electrical contact. The bottom side of the beam 20 at the hole is slightly concave (not shown).

This construction enables slight movement of the lens 12 in all directions.

Figure 4B:
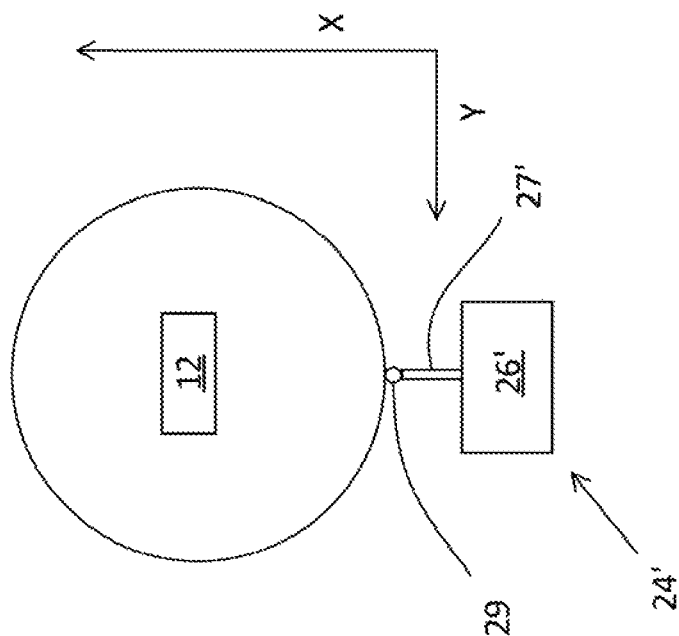
FIG. 4b schematically illustrates an alternative embodiment of a manipulator system comprising a ball joint.
Figure 4A:
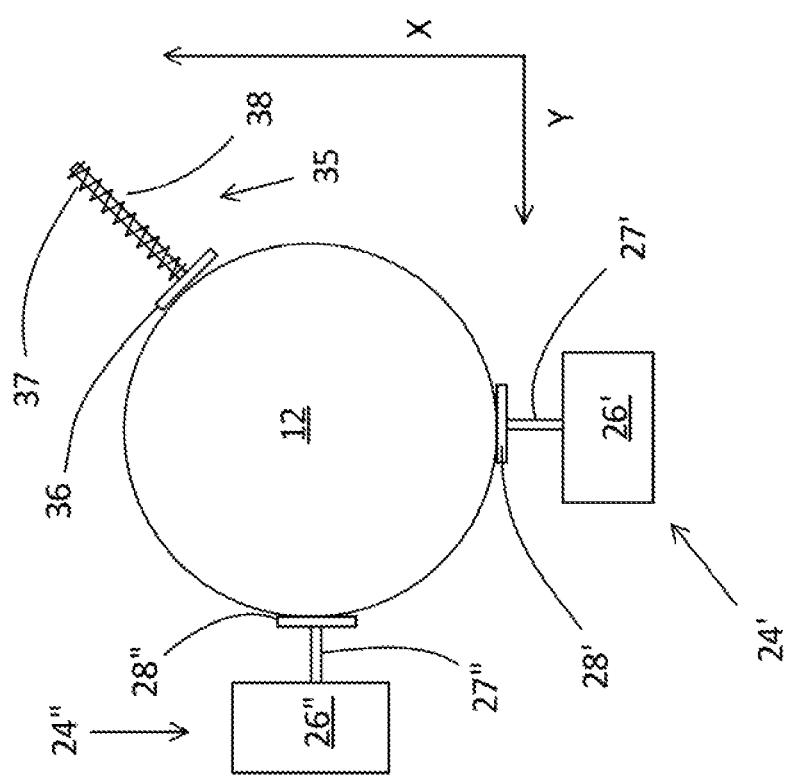
FIG. 4a schematically illustrates a manipulator system for tilting the lens in at least one coordinate direction.

FIG. 4a shows the device for enabling tilting of the lens in at least one direction.

Apart from one vertically oriented mechanism 24', which can move the lens 12 in the X direction, there can also be provided a horizontally arranged mechanism 24'' for moving the lens 12 in the Y direction. There is also provided a spring loaded support device 35. It comprises a support plate 36, a guide rod 37 attached to the frame-work (not shown) so as to be slidable, and a spring 38 exerting a pressing force on the support plate 36. This device 35 keeps the lens 12 in contact with the tilting mechanisms 24', 24''.

In operation the control unit 28 will perform a number of actions such as defining the energy E and the angle $\Theta_x$ by setting the energy, setting the lens voltages, setting voltages on the deflectors 14a, 14b. The motor will be energized such that the lens is tilted incrementally to a defined extent T which can be fractions of millimeters per increment, and where the maximum tilt T is a few mm, i.e. about maximum ±10 mm, as shown in FIG. 2.

When these actions have been performed an exposure is carried out whereupon the procedure is repeated for a new set of values for energy E and the angle $\Theta_x$.

Thus, an image (2D) is built by a stepwise procedure where a plurality of exposures are carried out by the detector.

This procedure of setting the motor increments in relation to the deflector voltages will be referred to as the tilting mechanism (i.e. motor and actuator rod) being operated synchronously with the deflection of the beam.

In FIG. 4b an alternative embodiment is illustrated.

It comprises a ball joint 29 (spherical bearing), i.e. a ball, suitably of metal although other materials may be usable, mounted (enclosed) in a socket attached to the lens body.

Using a rigid rod 27' actuated by a motor 26' as shown restricts this embodiment to movement in one coordinate direction (X direction).

Now the actual control of the synchronous operation will be briefly described.

Figure 5:
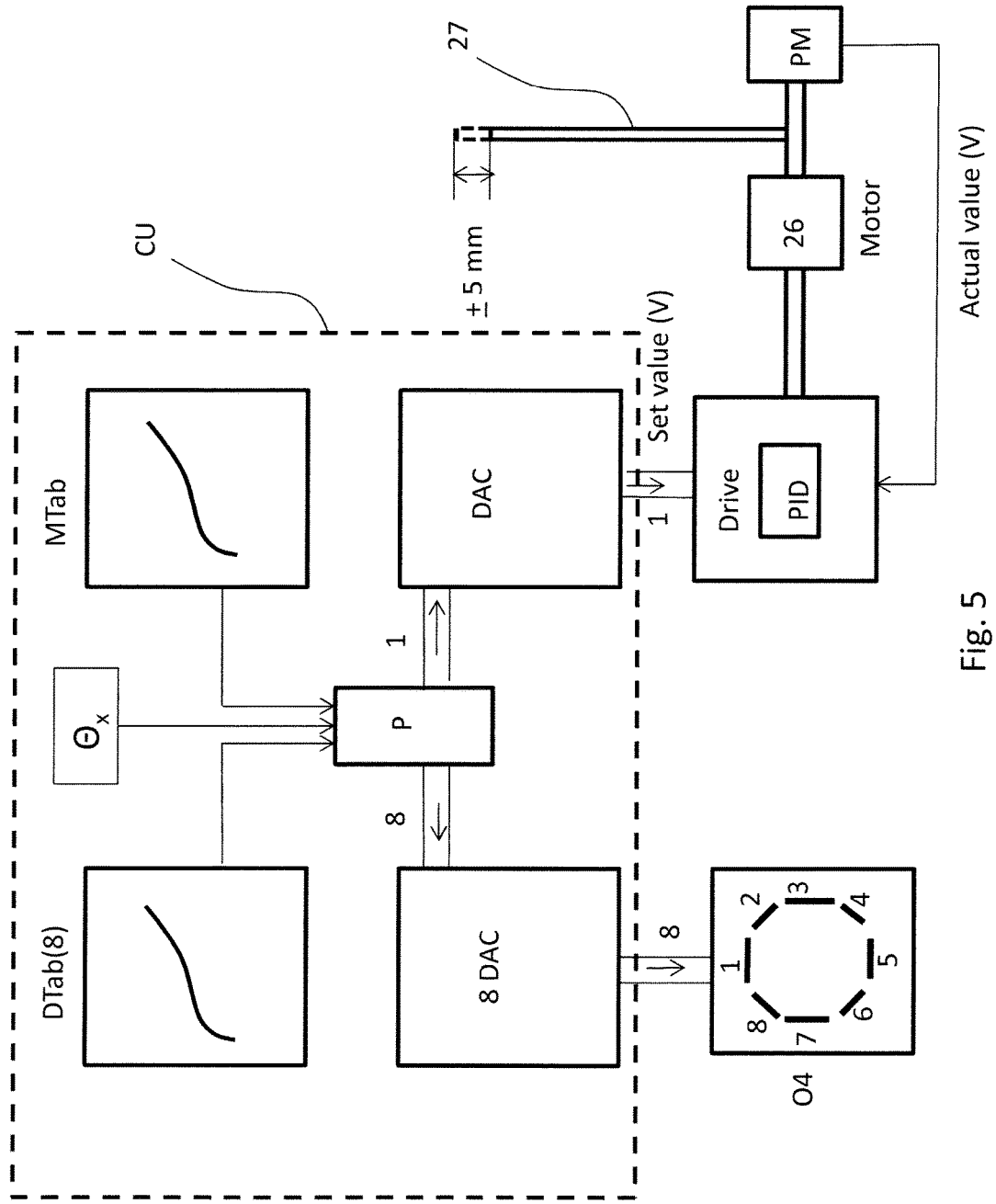
FIG. 5 schematically illustrates the control system.

FIG. 5 schematically illustrates the control.

A control unit CU, schematically indicated by a box drawn with broken lines, comprises memory units for storing data, and digital to analog converters DAC for the lens voltages and for the motor drive, respectively, comprising a processor P configured to retrieve data from memory, said data being converted to analog signals for setting voltages to deflectors and for actuating a motor in the tilting mechanism synchronously with the voltage settings Thus, the setting of parameters is done by providing data from tables DTab(8) memory of the control unit CU. Corresponding tables MTab are provided for the incremental operation of the motor. There are provided a plurality of DAC (Digital to Analog Converters), one for each deflector plate 1-8 in the element O4 (octopolar configuaration).

In the same manner there is a DAC for the motor drive.

The tables DTab(8) and MTab, respectively, contains voltage values corresponding to every start angle $\Theta_x$ for the electrons that are to be scanned. Thus, the tables contains values which are a function of said start angles $\Theta_x$.

As already indicated above, a complete scan cycle comprises a) setting voltages for the deflection for a given start angle $\Theta_x$ and b) a voltage (Set value (V)) corresponding to a desired movement of the lens, by running the motor and in response thereto movement of the rod 27 (same element as in FIG. 1), and c) repeating a) and b) for all angles $\Theta_x$, from e.g. −5° to +5°.

Coupled to the motor is a potentiometer PM that will yield a voltage (Actual value) in response to the rotation of the motor axis, and when the Actual value=Set value the PID will cause the motor to stop, and an exposure is made.

Now the operation of a system incorporating the novel tilt mechanism will be described.

FIG. 6a schematically shows an electron beam emanating from an emitting sample spot and how the beam is affected by a simplified lens. Each dot represents a point on the lens through which an electron beam passes and is refracted, i.e. the spots where the beam changes direction. In this simplified illustration a single lens element with focus on the slit at the right end is shown. As can be clearly seen in this simplified figure, electrons running in a straight line, i.e. at a start angle of 0° will be focused on the slit and enter the measurement region in a straight line, whereas electrons having a start angle >0° (e.g. 15°) will be focused on a different spot.

In FIG. 6b a deflector has been introduced. As can be seen the deflection results in the electrons taking a direction that deviates from the horizontal and misses the slit.

Figure 7A:
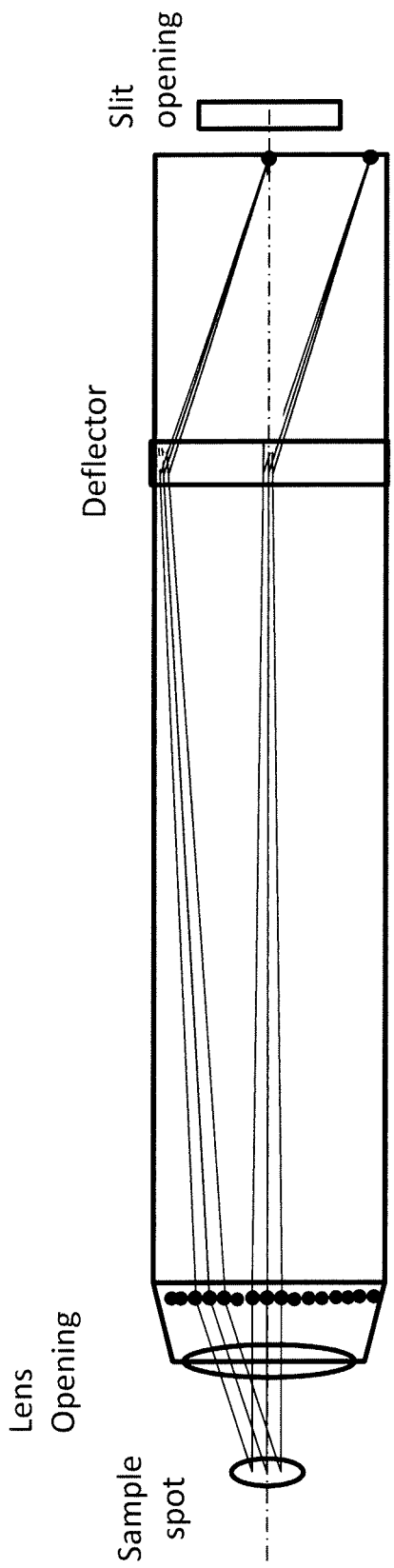
FIG. 7a shows the particle beams in a lens with a deflector but no tilt.
Figure 7B:
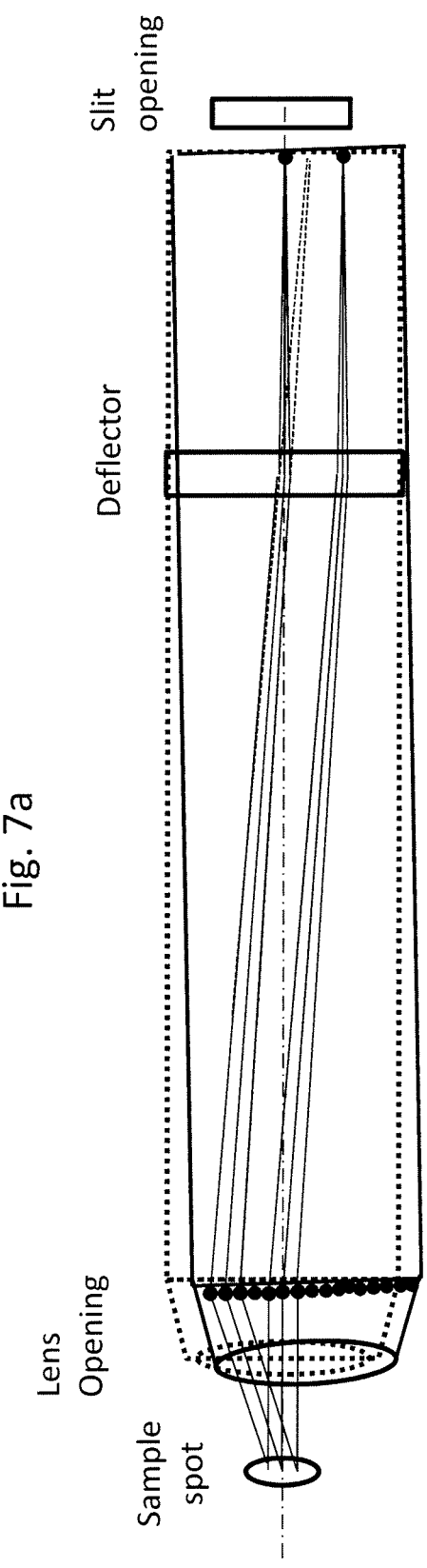
FIG. 7b shows the particle beams in a lens with a deflector with tilt.

FIG. 7a, which is the same as FIG. 6b, is to be compared with FIG. 7b wherein the lens is tilted (un-tilted position in broken lines) and the deflector is activated (electron beam shown by solid lines).

The broken beam lines in FIG. 7b (as a continuation of the solid electron beam lines) show the electron beam if the deflector is not activated. It is important to recognize that the tilting of the lens must be sufficient that the focus without deflection hits the slit member at a point below the slit. When the deflector is activated it is redirected to a horizontal pathway so as to hit exactly on the slit and enters the measurement region.

It is important to recognize that the tilting of the lens is a compromise. What one would wish to achieve is to move the entire lens vertically. This is certainly possible, but would however be more complicated since the lens is bulky (800 mm long) and arranged inside a vacuum chamber. Instead a very slight tilting of the lens achieves the same effect since the tilt angle is so small that it can be disregarded and for all practical purposes it is equivalent to a vertical translational movement of the lens. It would be equally possible to move the sample, i.e. a relative movement of sample/lens but again, the sample is attached to a very bulky structure, and moving it is complicated.

A mechanism for moving the entire lens is shown in FIG. 10 and described further below.

A further possibility would be to bend the lens. In practice the lens is made up from a plurality of segments, and it would be possible to actually cause a slight bend at a joint between two segments. Such bending would of course for all practical purposes be equivalent to a tilting as disclosed herein. Such bending is shown in FIG. 11 and described further below.

Thus, in generic terms one can say that at least a part of the lens is displaced (or moved) in a desired coordinate direction.

In FIG. 7b it is clearly seen that tilting and deflecting in a synchronous manner will cause the electrons to enter the slit essentially along the horizontal axis. The very small deviation of the lens from the horizontal due to the tilting is negligible. The lens is in the order of 800 mm long and the maximum deflection at the lens opening is 5 mm, in a normal case 1-2 mm.

An analogy from optics of how the system works can be to imagine an image being focused by a single lens on a screen on a given spot. If the lens is moved in one direction the light will enter the lens off-center, and as a consequence the image will also move on the screen. In order to bring the image back to the center one could place a prism between the lens and the screen. The prism "deflects" the light in a parallel manner, which is exactly what the deflector does to the electron beam.

Figure 8:
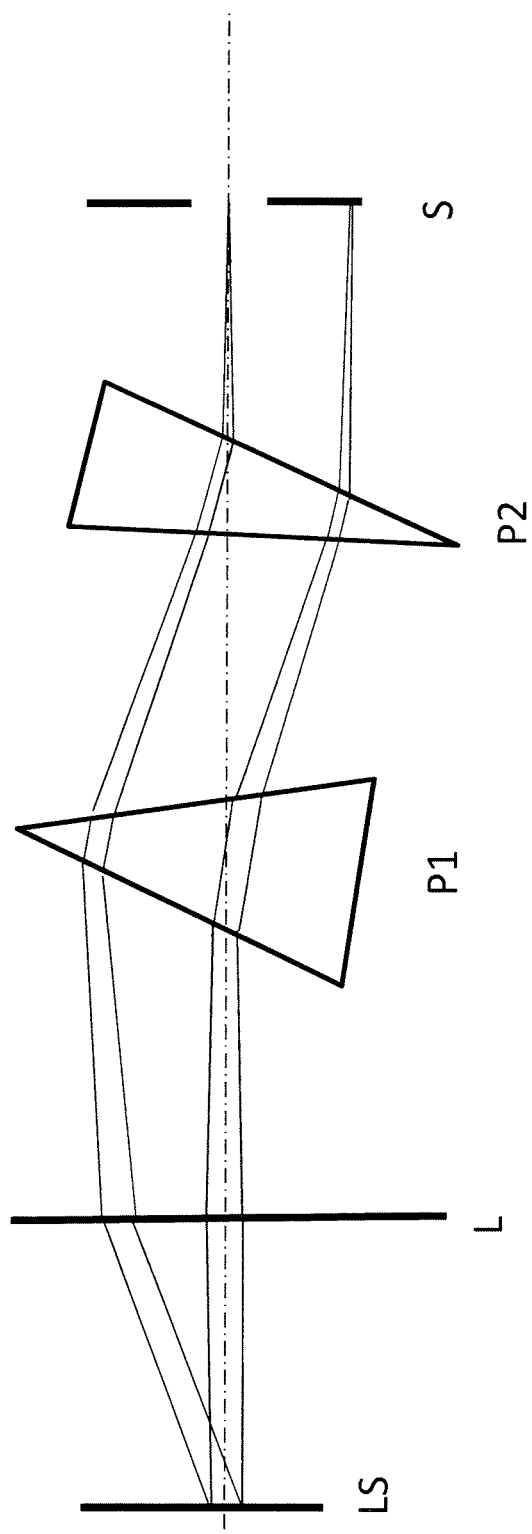
FIG. 8 illustrates double deflection of light using prisms.

A situation similar to the prior art using two deflections by using two prisms P1, P2 is shown in FIG. 8. Thus, light from a light source LS having a start angle of about 15°, and focused by a lens L will be refracted a first time P1 so as to point to a point below the slit S and a second time P2 to enter the slit S.

In FIG. 9 a situation analogous to the invention, i.e. moving the lens and performing one deflection.

FIG. 9a shows a light emitted from a light source LS is shown. The light is focused by a lens L and refracted by a prism P2. As can be seen the light passes the slit S at an angle.

FIG. 9b shows a situation where the lens L has been moved downwards a small distance (e.g. 2 mm) as indicated by the arrow. Thus, the light will be focused—differently since now the optical axis is displaced too. Therefore the prism P2 if positioned properly will refract (deflect) the light to align it to be parallel with the optical axis.

This is completely analogous to the situation in FIG. 7b.

In FIG. 10 one of the alternative mechanisms for displacing the optical axis is schematically shown, namely a mechanism for displacing the entire lens vertically.

Thus, the lens 12 in the shown embodiment is suspended by two support structures, e.g. rods 27 like in the embodiment shown in FIG. 1, via a support plate 28. Of course a ball joint type suspension 29 would be equally applicable in this embodiment. The rods are actuated by motors 26.

FIG. 10 a shows the lens 12 in a "nominal position". In FIG. 10b the motors 26 have withdrawn the rods 27 such that the lens 12 has been moved slightly in the vertical direction, a distance D, as illustrated by the arrow A.

FIG. 11 schematically illustrates an embodiment wherein the lens is subdivided in two segments via a joint 110 at some point along the lens 12. The ends of the lens must be pivotally suspended. Thus, this embodiment allows the segments to be moved at the joint 110 with respect to the optical axis. FIG. 11a is the "nominal" position and FIG. 11b shows the bent situation (slightly exaggerated), i.e. the part of the lens 12 at the joint 110 has been displaced a distance D'.

The mechanism enabling this movement can be the same or similar to what is shown in FIG. 10, although ball joints may be preferable in this embodiment.

The invention described above will now be further illustrated in terms of its function compared to the prior art solution according to Scienta. The novel solution is based on the inherent properties of the lens, and is illustrated in FIGS. 12-16.

Figure 12:
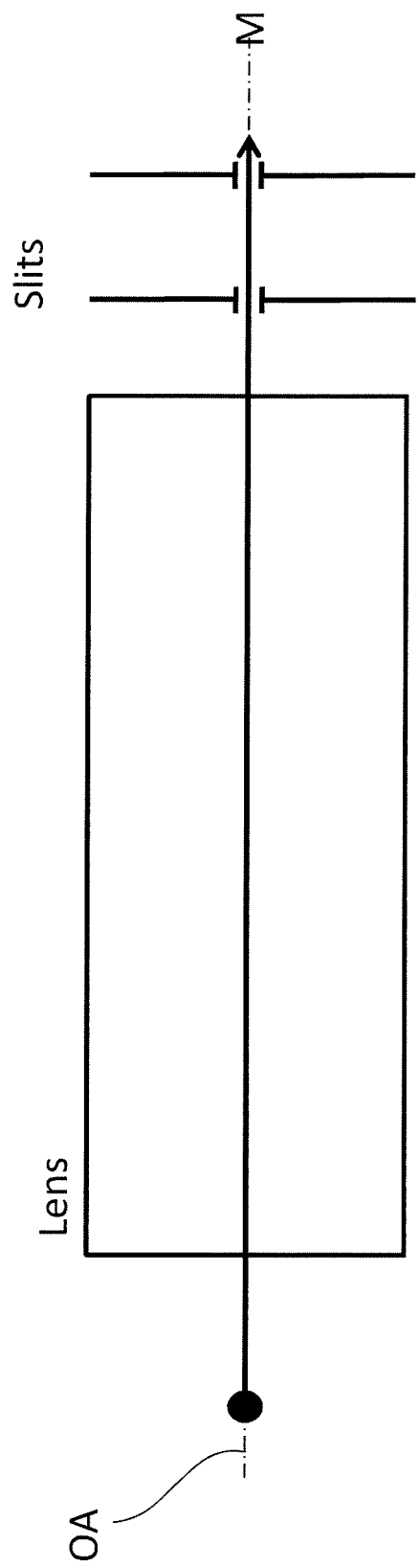
FIG. 12 schematically illustrates a straight beam running through a lens.

FIG. 12 shows an electron beam emitted from the sample ● at angle "0". It goes straight through the lens along its optical axis OA and enters the slits and goes through both slits and into the measurement region M.

Figure 13:
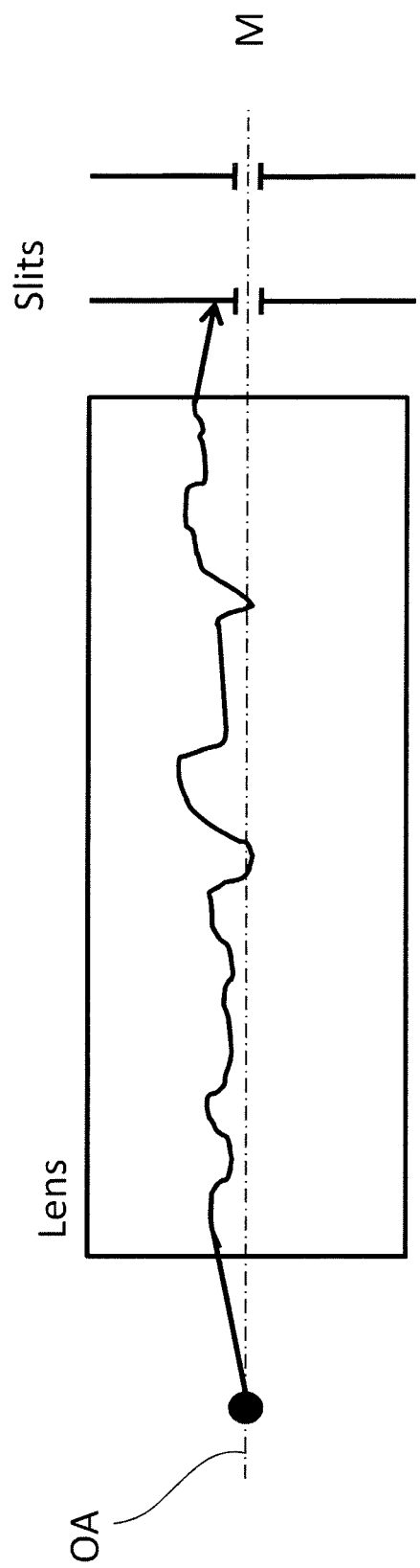
FIG. 13 schematically illustrates a beam emitted at an angle from the sample and running through a lens.

FIG. 13 shows what happens for an electron beam that is emitted from the sample at an angle. It goes through the lens but exits at a different location and misses the slits. The trajectory inside the lens is illustrated with a seemingly random curve, simply for illustrating the complexity of the lens.

Figure 14:
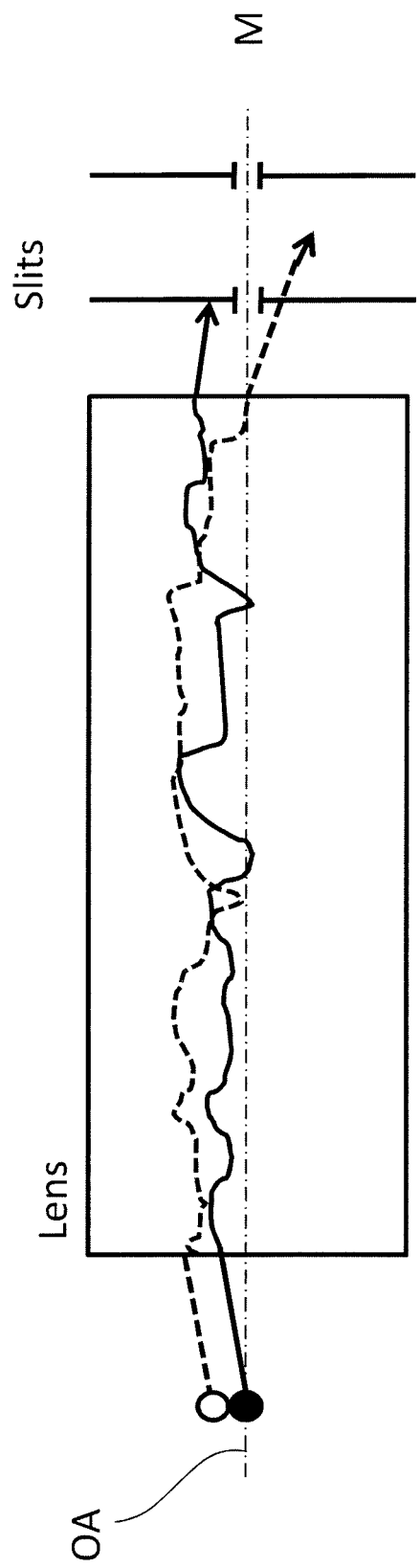
FIG. 14 schematically illustrates where a beam emitted at an angle from the sample and running through a lens crosses the optical axis.
Figure 15:
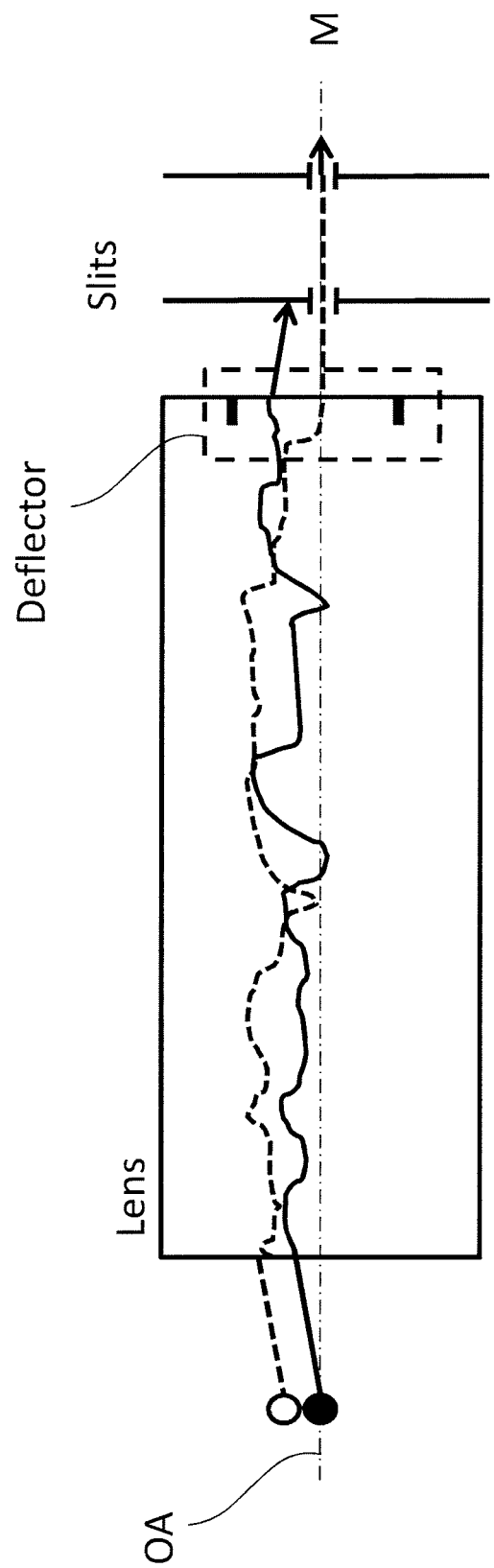
FIG. 15 schematically illustrates deflection of a beam as shown in FIG. 14.

In FIG. 14 the sample has been moved (symbolized with ◯) to a slightly off-set position. The electron beam will again miss the slits but if the sample is moved appropriately, it exits the lens at a point where it crosses the optical axis. Therefore, one single deflector, provided at the exit end of the lens at the slits, will deflect the beam to go through the slits along the optical axis into the measurement region, see FIG. 15.

Figure 16:
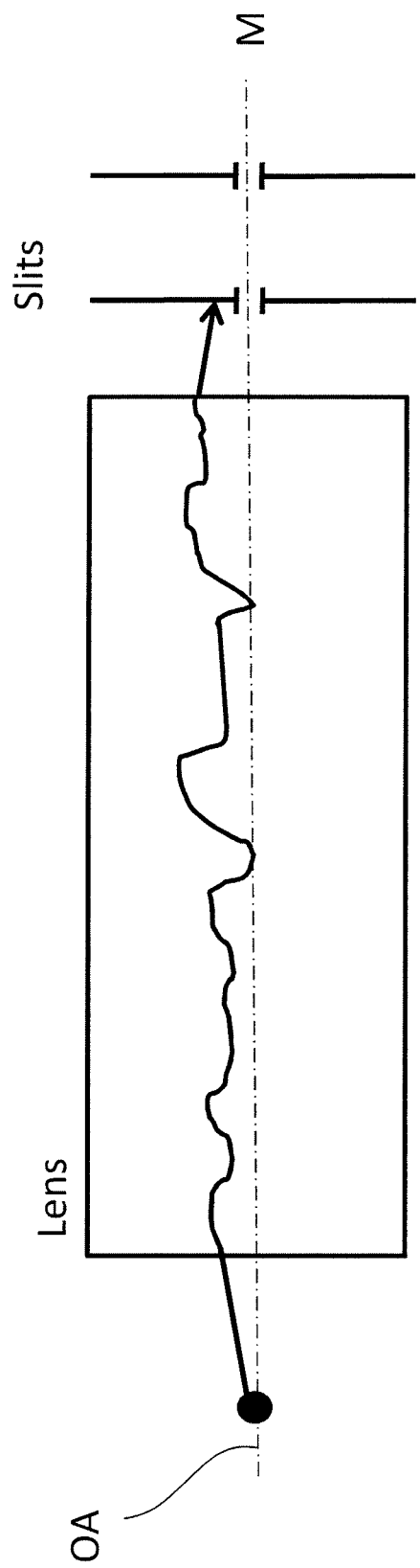
FIG. 16 schematically illustrates the same situation as in FIG. 13.
Figure 17:
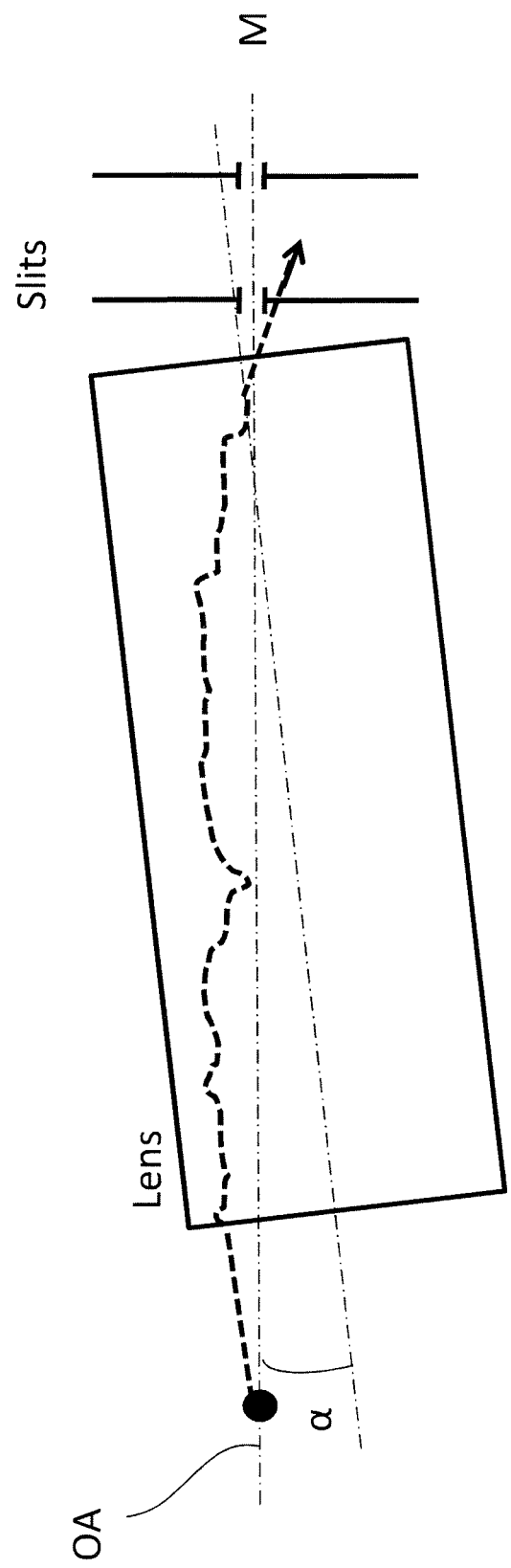
FIG. 17 schematically illustrates the effect of tilting the lens from a position shown in FIG. 16.

Now, moving the sample is equivalent to moving the lens, or as shown in FIGS. 16 and 17, tilting the lens a small angle α from the horizontal position shown in FIG. 16 to the tilted position in FIG. 17. Tilting is much simpler than moving the entire lens, and the angles involved are so small that the result will be virtually the same as if the entire lens had been moved, and will not have any significance for the purpose of explaining the effect of the invention.

Thus, if the lens is tilted appropriately the beam will exit the lens near the slits and will cross the original optical axis OA, i.e. the axis running through pair of slits.

Figure 18:
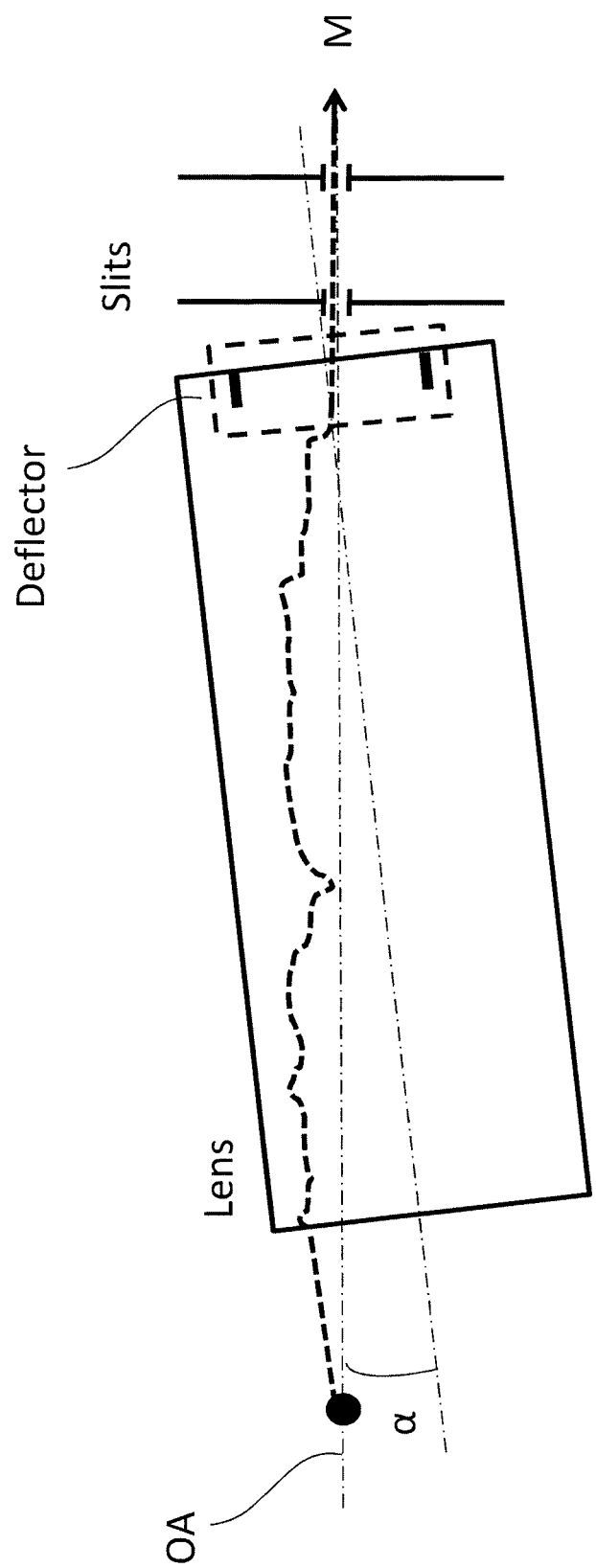
FIG. 18 schematically illustrates deflection of a beam in the situation shown in FIG. 17.

If a single deflector is now provided (as previously shown in FIG. 15), the beam can be brought back in line with the original optical axis OA, and will run through the slits into the measurement region M, see FIG. 18.

Figure 19:
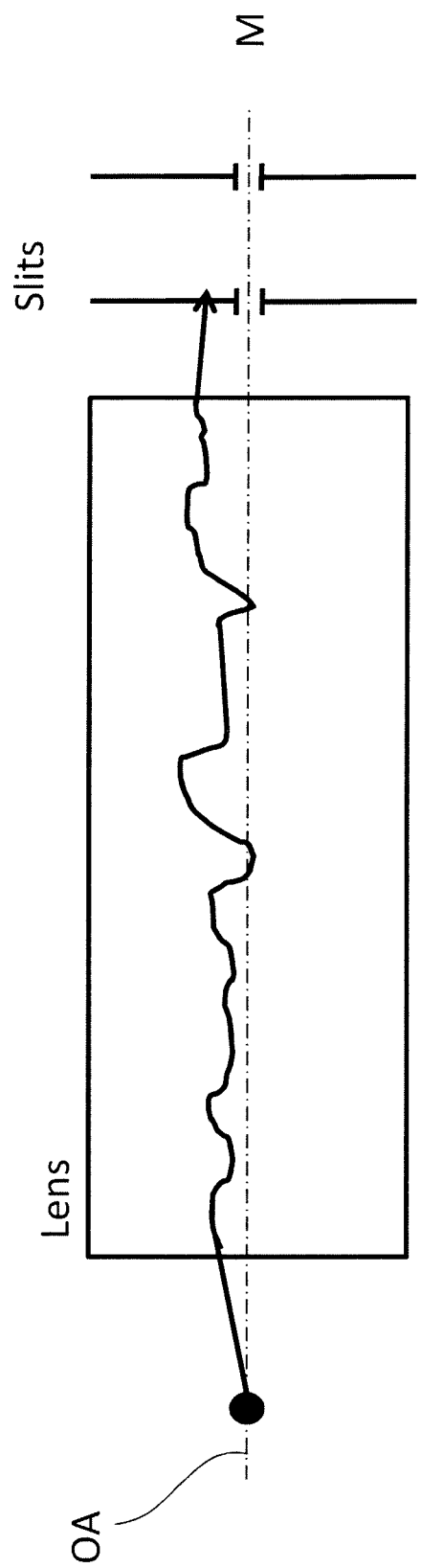
FIG. 19 schematically illustrates the prior art system according to WO 2013/133739 without deflection.
Figure 20:
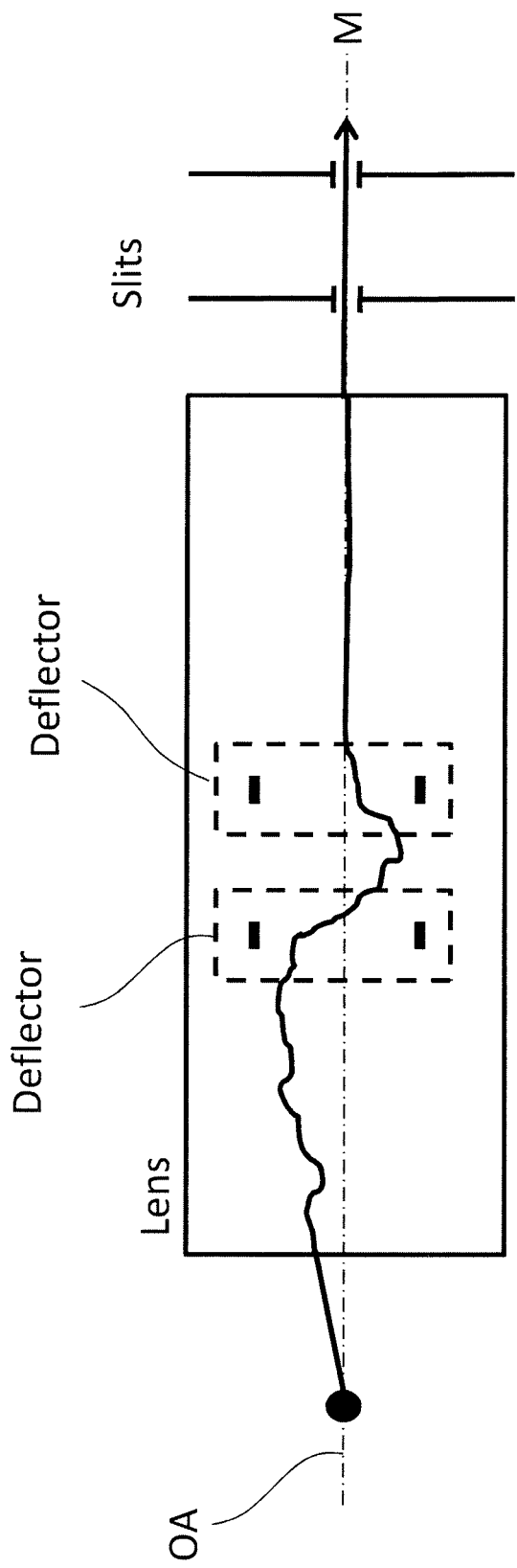
FIG. 20 schematically illustrates the prior art system according to WO 2013/133739 with two deflections.

For comparison, what Scienta does is in its publication WO 2013/133739 is illustrated in FIGS. 19 and 20.

Starting from the same situation as in FIG. 12, shown in FIG. 19, Scienta provides two deflectors which change the beam trajectory such that it finally reaches the slits in alignment with the optical axis, FIG. 20.

Figures 21A, 21B:
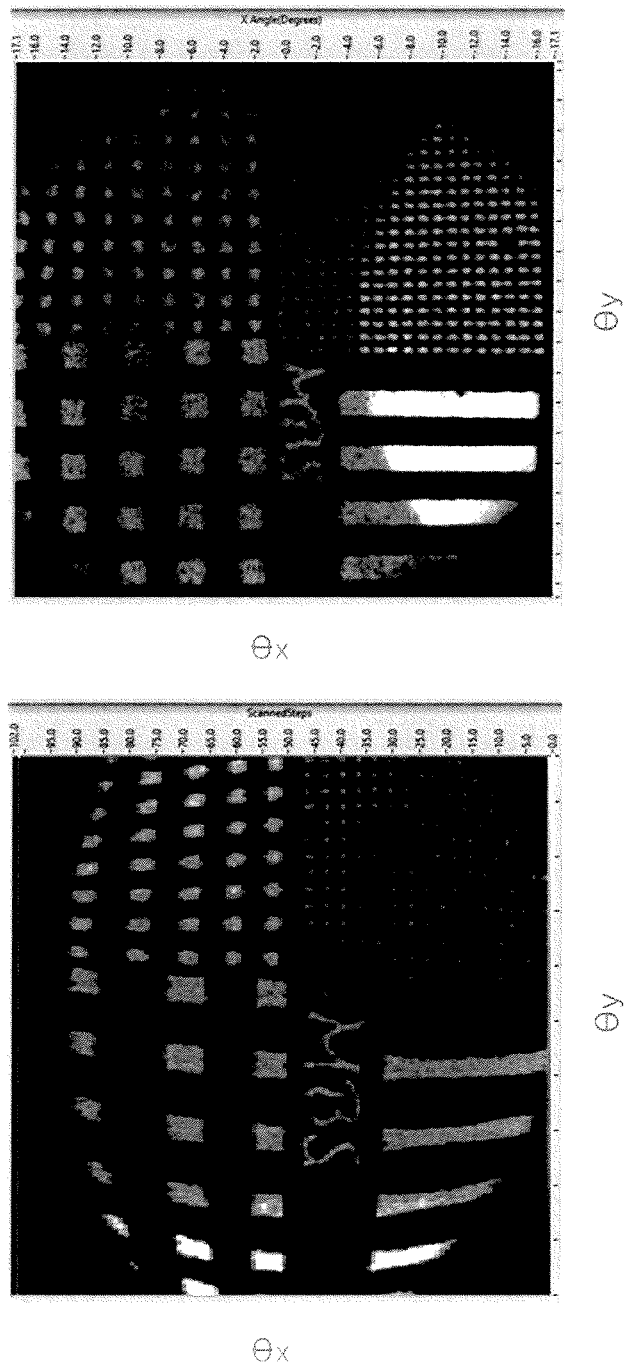
FIG. 21a shows the recorded image obtained by the prior art system.
FIG. 21b shows the recorded image obtained by the present system.

FIGS. 21 (a) and (b) show a comparison of the recorded images obtained by the prior art system and by the present system. FIG. 21 (a) is the recorded image obtained by prior art system with double deflectors. Similar to the electron spectrometers according to WO 2013/133739 by Scienta, the prior art system includes double deflectors. FIG. 21 (b) is the recorded image obtained by the present electron spectrometer with the angle correction lens. The record image shown in FIG. 21 (b) is significantly less distorted compared to the recorded image shown in FIG. 21 (a).

The invention claimed is:

1. A charged particle spectrometer of hemispherical analyzer type for analyzing a particle emitting sample, the spectrometer comprising:
   a measurement region having an entrance configured to allow particles to enter the measurement region;
   a lens system for forming a particle beam of the charged particles and transporting the particles between the particle emitting sample and the entrance of the measurement region, the lens system having a substantially straight optical axis;
   a deflector arrangement in the lens configured to deflect the particle beam in at least one coordinate direction perpendicular to the optical axis of the lens system before entrance of the particle beam into the measurement region,
   a detector arrangement for detecting the positions of the charged particles in the measurement region, the detector arrangement being configured to determine the positions of the charged particles in two dimensions, one of which is indicative of the energies of the particles and one of which is indicative of the start directions or start positions of the particles, and
   at least a first mechanism configured to displace at least a part of the lens with respect to an axis extending between the particle emitting sample and the analyser entrance in at least a first coordinate direction synchronously with a deflection of the particle beam.

2. The charged particle spectrometer according to claim 1, wherein the lens is suspended in a multidirectional pivot point at an end of the lens that is adjacent to the entrance of the measurement region such that the lens can be tilted around the pivot point in the coordinate direction, and wherein the mechanism for moving at least the entrance region of the lens system is a first tilting mechanism.

3. The charged particle spectrometer according to claim 2, wherein the mechanism for tilting the lens comprises a motor, an actuator rod connected to the motor, and a spring loaded device arranged to keep the lens in contact with the first tilting mechanism.

4. The charged particle spectrometer according to claim 2, comprising a second tilting mechanism arranged at right angles to the first tilting mechanism and configured to tilt the lens in a second coordinate direction synchronously with a deflection of the particle beam, and wherein the spring loaded device is arranged symmetrically opposite the first and second tilting mechanisms at an angular distance of about 135°.

5. The charged particle spectrometer according to claim 2, further comprising a control unit, comprising a processor configured to retrieve data from a memory, the data being converted to analog signals corresponding to voltage settings for the deflector and for actuating a motor in the tilting mechanism synchronously with the voltage settings.

6. The charged particle spectrometer according to claim 5, wherein the data is provided as tables, one set of tables for each of a plurality of deflector plates in the deflector arrangement, and one table for the motor, wherein a specific voltage setting correlates to a specific motor setting to provide a specific tilting of the lens.

7. The charged particle spectrometer according to claim 1, wherein the mechanism for moving at least a part of the lens with respect to the axis between the particle emitting sample and the analyser entrance in at least a first coordinate direction is a mechanism that moves the entire lens in the coordinate direction.

8. The charged particle spectrometer according to claim 1, wherein the mechanism for moving at least a part of the lens with respect to the axis between the particle emitting sample and the analyser entrance in at least a first coordinate direction is a mechanism that bends the lens in the coordinate direction.

9. The charged particle spectrometer according claim 1, wherein the mechanism for moving at least a part of the lens comprises a ball joint connecting an actuator rod to a lens body.

10. A method for operating a charged particle spectrometer of hemispherical analyzer type in angular mode, the method comprising:
   operating a deflector arrangement inside a lens system to deflect an electron beam emitted by a particle emitting sample as the electron beam passes through the lens system; and
   moving at least a part of the lens with respect to an axis between the particle emitting sample and an analyser entrance in at least a first coordinate direction in a desired coordinate direction synchronously with the deflection of the particle beam by the deflector arrangement.

11. The method of claim 10, wherein operating the deflector arrangement comprises changing a voltage applied to the deflector arrangement.

12. A method for determining at least one parameter related to charged particles emitted from a particle emitting sample, the method comprising:
   forming a particle beam of the charged particles and transporting the particles between the particle emitting sample and an entrance of a measurement region by means of a lens system having a substantially straight optical axis;
   deflecting the particle beam in at least a first coordinate direction perpendicular to the optical axis of the lens system before entrance of the particle beam into the measurement region;
   detecting the positions of the charged particles in the measurement region, the positions being indicative of the at least one parameter, wherein the detecting the positions of the charged particles comprises detection of the positions in two dimensions, one of which is indicative of the energies of the particles and one of which is indicative of the start directions or start positions of the particles; and
   displacing at least a part of the lens with respect to the axis between the particle emitting sample and the analyser entrance in the coordinate direction synchronously with the deflection of the particle beam, whereby the trajectories of the charged particles will enter the measurement region.

13. The method according to claim 12, wherein the lens is suspended in a multidirectional pivot point at an end of the lens that is adjacent to the entrance of the measurement region, and comprising tilting the lens in the coordinate direction.

14. The method according to claim 12, wherein displacing at least a part of the lens comprises moving the entire lens.

15. The method according to claim 13, wherein displacing at least a part of the lens comprises bending the lens at least one point.

16. The method according to claim 14, wherein displacing at least a part of the lens comprises incrementally displacing at least a part of the lens.

* * * * *